United States Patent [19]

Yoo

[11] Patent Number: 4,895,679
[45] Date of Patent: Jan. 23, 1990

[54] PROCESS FOR PRODUCTION OF CHENODEOXYCHOLIC ACID AND NOVEL INTERMEDIATES USEFUL FOR THE PROCESS

[75] Inventor: Seo H. Yoo, Wyckoff, N.J.

[73] Assignee: Prime Chemicals Technology Corporation, Wyckoff, N.J.

[21] Appl. No.: 331,975

[22] Filed: Feb. 17, 1989

[51] Int. Cl.$^4$ ................................................ C07J 1/00
[52] U.S. Cl. .................................................... 260/397.1
[58] Field of Search ...................................... 260/397.1

[56] References Cited

PUBLICATIONS

J. Organic Chemistry; vol. 24; pp. 1367–1368, (Sep. 1959); Sato, et al.

Primary Examiner—Joseph A. Lipovsky
Attorney, Agent, or Firm—Burns, Doane, Swecker & Mathis

[57] ABSTRACT

Novel intermediates useful in the synthesis of chenodeoxycholic acid, the intermediates being of the formula:

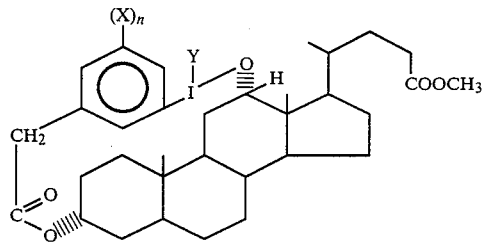

wherein —X is an electron withdrawing group, n is an integer equal to zero or one, and —Y is a halogen.

A process for producing such novel intermediates from 5$\beta$-cholanic acid-3$\alpha$, 7$\alpha$, 12$\alpha$-triol methyl ester is carried out without using highly toxic and carcinogenic compounds such as dichromates and chromium trioxide.

13 Claims, No Drawings

PROCESS FOR PRODUCTION OF CHENODEOXYCHOLIC ACID AND NOVEL INTERMEDIATES USEFUL FOR THE PROCESS

BACKGROUND OF THE INVENTION

The present invention relates to the preparation of chenodeoxycholic acid, and, more particularly, to certain novel intermediates as well as to a novel process employing such intermediates in the preparation of chenodeoxycholic acid.

Chenodeoxycholic acid is one of the two primary bile acids in man and, in fact, is the key raw material in the ursodeoxy cholic acid synthetic pathway. Recently, it has attracted a great deal of attention from the pharmaceutical industry by virtue of its usefulness in the treatment of gallstones. More specifically, in clinical studies conducted with patients suffering from gallstones, it was observed that about 60% of the patients treated with chenodeoxycholic acid exhibited a reduction in the number of gallstones produced. Ursodeoxycholic acid, which as indicated above is a derivative of chenodeoxy-cholic acid, is also useful in the treatment of gallstones as well as for aiding the liver function generally.

Although recognized as a useful compound, the synthesis of chenodeoxycholic acid has been fraught with difficulties. Specifically, the structure of chenodeoxycholic acid is as follows:

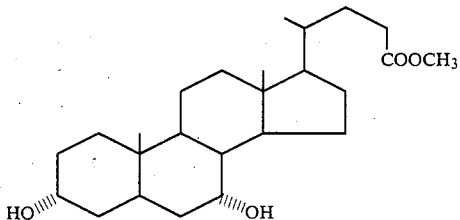

It is noted in the above formula that the compound has hydroxy groups at its number 3 and 7 positions. One of the problems which has been encountered in the synthesis of the above compound is that the typical starting reagent namely, 5β-cholanic acid-3α,7α,12α-triol methyl ester has hydroxy groups at not only the number 3 and 7 positions, but also at the number 12 position and it is very difficult to selectively eliminate such number 12 hydroxy without also adversely affecting the desired number 3 and 7 hydroxy groups. This is especially true with respect to the differentiation between the hydroxy groups at the number 7 and 12 positions which are virtually indistinguishable in terms of their reactivity with most conventional oxidation agents.

The art has developed a number of synthetic processes in an attempt to differentiate among the various hydroxy groups. Thus, in the procedure described by Sato and Ikekawa in "Preparation of Chenodeoxychloic Acid", J. Organic Chemistry, Volume 24, pp. 1367-8 (September 1959), methyl cholate 3,7-diacetate was oxidized with Kiliani's reagent (a solution of 53 g of chromium trioxide and 80 g of concentrated sulfuric acid in 460 g of water) in acetone to the 12-oxo derivative. After conversion to the corresponding 12-thioketal with ethanedithiol, it was desulfurized successfully with Raney nickel to the acetate methyl ester of chenodeoxycholic acid. Subsequent hydrolysis of the acetate methyl ester yielded chenodeoxycholic acid of high purity.

Another process for producing chenodeoxycholic acid is set forth in Pharmazeutische Wirkstoffe, by Von A. Kleemann and J. Engel, Georg Thieme Verlag Stutgart pp. 181-182 (1982) wherein 5β-cholanic acid-3α,-7α,12α-triol methyl ester is formed from the corresponding carboxylic acid by reaction with methanol and sulfuric acid. The methyl ester is then reacted with acetic anhydride in the presence of pyridine to yield methyl cholate 3,7-diacetate. It is then necessary to selectively oxidize the hydroxy group at the number 12 while leaving the acetoxy groups at the number 3 and 7 positions intact. This is achieved by reacting the methyl cholate 3,7-diacetate with sodium dichromate and acetic acid to yield the 12-oxo derivative which, upon further reaction with hydrazine and HOCH$_2$—CH$_2$OH followed by HCl yields the desired chenodeoxycholic acid.

A number of disadvantages exist with the above-described synthetic routes. In the first place, the initial step of esterifying only the number 3 and 7 hydroxy groups but leaving the number 12 hydroxy intact, while theoretically attractive, has not proven completely satisfactory in practice in view the fact that some of the hydroxy groups at the number 12 position are indeed esterified. Such esterified groups, of course, will not react in the subsequent oxidation step. Furthermore, it is noted that even where esterification occurs as desired, i.e., only at the number 3 and 7 positions so that the number 7 hydroxy can be selectively oxidized, the removal of such ester group, especially at the number 6 carbon, is quite difficult to carry out in practice. Not surprisingly, in light of the undesirable side reactions which occur in the above-described synthetic processes, there will be present with the desired product a number of impurities which make it very difficult to obtain product crystals of high purity.

Perhaps the most significant disadvantage of the above processes concerns the chromium trioxide or the dichromates themselves, which are very dangerous to handle since they are both highly toxic and suspected carcinogens which, of course, must be kept isolated from workers and disposed of very carefully and with great cost.

Nonetheless, despite the environmental hazards and the costs associated with selective chromium dioxide and dichromate salts oxidation, the art continues to employ such technique as the preferred synthetic route in view of the lack of viable alternatives.

SUMMARY AND OBJECTS OF THE INVENTION

In view of the foregoing limitations and shortcomings of prior art processes for the synthesis of chenodeoxycholic acid as well as other disadvantages not specifically mentioned above, it should be apparent that there still exists a need in the art for a process which selectively oxidizes the number 12 hydroxy group of a 5β-cholanic acid-3α,7α,12α-triol methyl ester, in good yield, without the need for employing the highly undesirable reagents characterizing prior art synthetic techniques namely, dichromate and chromium trioxide. It is, therefore, a primary objective of the present invention to fulfill that need by providing novel intermediates as well as a novel process employing such intermediates for the synthesis of chenodeoxycholic acid from cholic acid methyl ester utilizing a non-hazardous compound which selectively oxidizes only the number 12 hydroxy of cholic acid methyl ester and not the number 7 hydroxy of cholic acid methyl ester. More particularly, it is an object of the present invention to provide a process for the synthesis of chenodeoxycholic acid from cholic acid methyl ester utilizing a non-hazardous compound having one end which esterifies the number 3 hydroxy of the cholic acid methyl ester and an opposite halogenated end which is capable of oxidizing the number 12 hydroxy but incapable of reacting with the number 7 hydroxy of cholic acid methyl ester.

A further object of the present invention is to provide a process for the preparation of chenodeoxycholic acid wherein the desired product is obtained in a high enough yield so as to obtain high purity product crystals.

Yet another object of the present invention is to provide a process for the preparation of chenodeoxycholic acid which employs starting materials, novel intermediates and reaction conditions which are highly safe and do not require special handling characterizing chromic acid and dichromate processes of the prior art.

Another object of the present invention is to provide a process for the preparation of chenodeoxycholic acid which can be carried out simply and with a high degree of reproducibility.

In a first aspect, the present invention relates to a process for producing a compound of the formula:

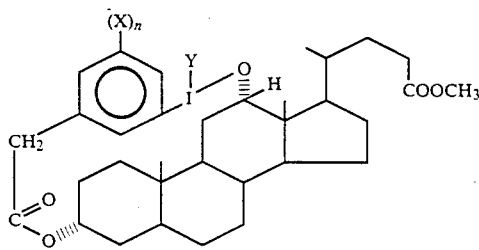

comprising the steps of:

(i) reacting 5β-cholanic acid-3α,7α,12α-triol methyl ester with a compound of the formula:

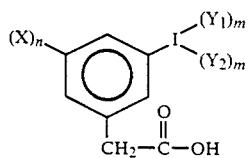

wherein —X is an electron withdrawing group, n is an integer equal to zero or one, —$Y_1$ and —$Y_2$, which are identical or different, are each a halogen, and m is an integer equal to zero or one;

there being formed, when m equals zero, a compound of the formula:

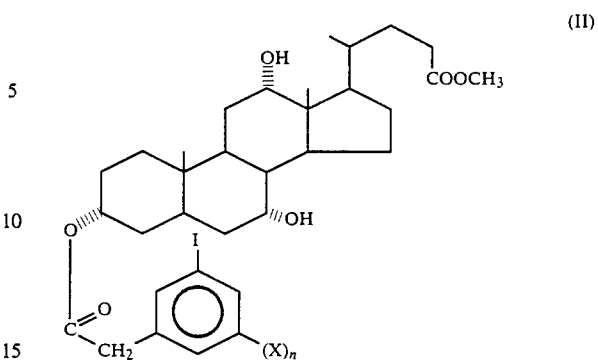

said compound (II) then being reacted with a halogen source to form a compound of the formula:

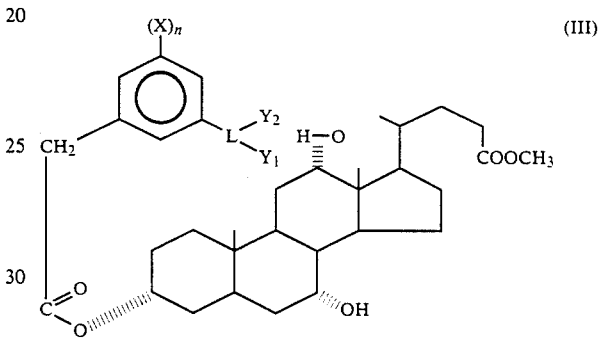

there being formed, when m equals one, said compound (III);

(ii) reacting the group —$Y_1$ or —$Y_2$ of said compound (III) with the number twelve carbon of said compound (III), in the presence of a solvent serving as an acid scavenger, to form said compound (IV).

In a second aspect, the present invention relates a novel intermediate in the synthesis of chenodeoxycholic acid and, more particularly, a compound of the formula:

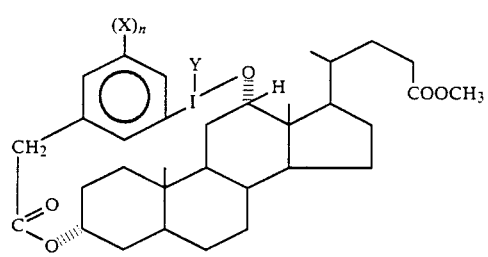

wherein —X is an electron withdrawing group, n is an integer equal to zero or one, and —Y is a halogen.

In a preferred embodiment, the compound (I) is an iodophenylacetylchloride which is converted in situ to the corresponding dichloroiodophenylacetylchloride with chlorine gas thereby avoiding exposure to the dichloroiodophenylacetylchloride.

With the foregoing and other objects, advantages, and features of the invention that will become hereinafter apparent, the nature of the invention may be more clearly understood by reference to the following detailed description of the invention and to the appended claims.

DETAILED DESCRIPTION OF PREFERRED EMBODIMENTS

1. Starting materials

To synthesize chenodeoxycholic acid in accordance with the present invention, 5β-cholanic acid-3α,7α,12α-triol methyl ester (cholic acid methyl ester), is reacted with an iodoacetylphenylhalide of the formula:

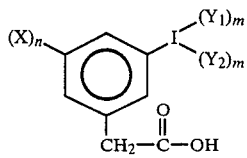

wherein —X is an electron withdrawing group, n is an integer equal to zero or one, —$Y_1$ and —$Y_2$, which are identical or different, are each a halogen, and m is an integer equal to zero or one. In a preferred embodiment, —$Y_1$ and —$Y_2$ are each chlorine and —X, when present, is either a halogen or —$NO_2$.

Cholic acid methyl ester itself is a known commercially available compound. Additionally, techniques are described in the literature for preparing cholic acid methyl ester from the corresponding carboxylic acid in the presence of methanol and sulfuric acid.

The iodophenylacetylhalides are also commercially available known compounds. For example, m-iodophenylacetyl chloride is available from Fairfield Chemical Company, Inc, Blythewood, S.C.

In reacting cholic methyl ester with iodophenylacetylhalides, there should further be employed an acid scavenger solvent such as pyridine and its derivatives or other known acid scavengers such as dimethylformamide.

2. Process Conditions

The reaction of cholic acid methyl ester with iodophenylacetyl chloride is now described. It will be appreciated, however, that any of the iodophenylacetyl halides described above may be substituted for iodophenylacetyl chloride. In the first step, cholic acid methyl ester and m-iodophenyl acetyl chloride, present in a ratio of about 1.00 to 1.05 are dissolved in an amount of solvent suitable to dissolve the reactants, i.e., enough solvent to form a solution containing up to about 10% solids. Any non-polar solvent which is non-reactive may be employed in accordance with the present invention such as benzene, toluene, etc. An acid scavenger such as pyridine should also be present since a mole of hydrochloric acid is generated for each mole of iodophenylacetyl chloride which reacts with cholic acid methyl ester. The mixture is preferably reacted at about room temperature. The reaction is complete within about two hours. The reaction proceeds as follows:

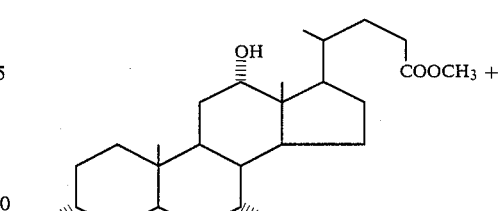

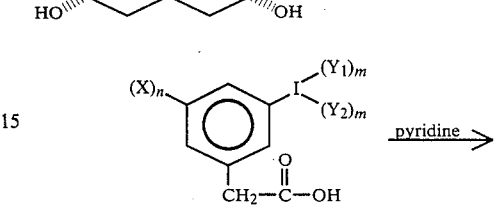

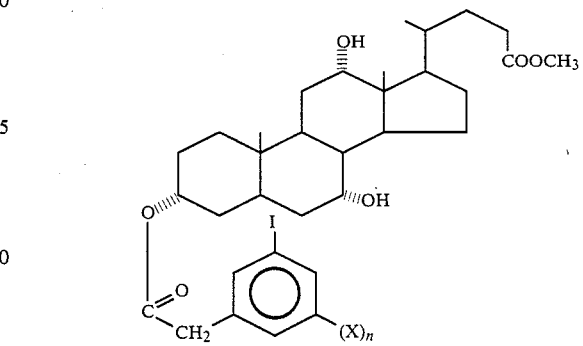

Methyl 3α-(m-iodophenyl acetoxy)-7α,12α-dihydroxy cholanate is thereby produced as an esterified product and is recovered upon removal of the solvent in, for example, a rotary evaporator.

Where m-iodophenylacetyl chloride is employed, it is necessary to react the above esterified product with a source of chlorine such as molecular chlorine in a non-polar, aprotic solvent, e.g., a chloro-solvent such as carbon tetrachloride. Specifically, the esterified product previously recovered is dissolved in an amount of carbon tetrachloride sufficient to completely dissolve the esterified product, i.e., so as to form an about 0.1 molar solution of the esterified product in carbon tetrachloride. Chlorine is then bubbled into the solution in an amount sufficient to chlorinate the iodo group which translates to about a molar amount of chlorine per mole of the esterified product. Such is carried out at a temperature between of about 0° C. and, once again, in the presence of a suitable acid scavenger as described above. Atmospheric moisture should be excluded.

The reaction mixture is allowed to stand at about room temperature for a period of time sufficient to chlorinate the iodo group. For this purpose, less than one hour is typically sufficient.

The esterified product thereby reacts with the molecular chlorine to form a chlorinated addition product as follows:

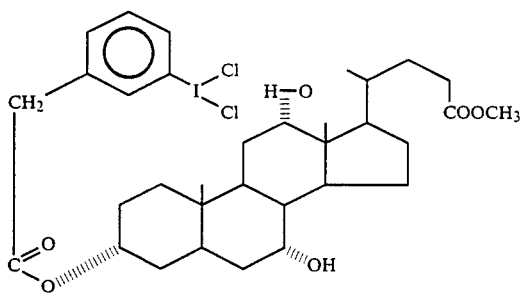

One of the terminal chlorine atoms of the chlorinated addition product, in the presence of an acid scavenger and a chloro-solvent as described above, then reacts with the number 12 hydroxy group of the ester product to produce, after elimination of hydrochloric acid, the following novel intermediate;

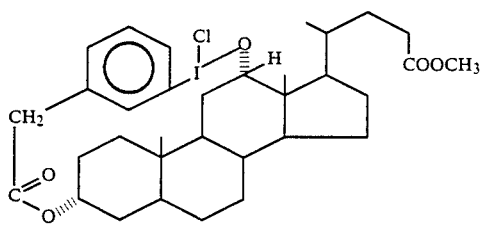

It is noted that the terminal chlorine of the chlorinated addition product reacts only with the number 12 hydroxy to form the oxidation product thereof and not with the number 7 hydroxy group. More specifically, the distance between the 3α-oxygen and the 12α-hydrogen is very close to the distance between the oxygen and the chlorine in the compound m-dichloroiodophenylacetate on chodanic acid. However, the distance between the 3α-oxygen and 7α-hydrogen is far shorter than both the distance between the 3α-oxygen and the 7α-oxygen on the ring and the oxygen and the chlorine in the iodophenyl compound. Accordingly, even though chemically the 7α- and 12α-hydrogens are virtually indistiguishable, the claimed process is completely selective for the 12α-hydrogen since the terminal chlorine is incapable of even reaching the 7α-hydrogen of the ring. Thus, using relatively mild reaction conditions, the 7α-hydrogen reacts with the chlorine as described in the reaction above and, after elimination of another hydrochloric acid, there results methyl 7α-hydroxy-3α-(m-iodophenylacetoxy)-12-oxo cholanate as follows:

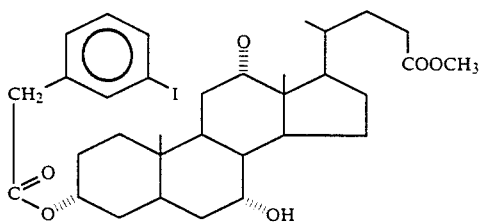

In practice, the chlorination of the esterified product, the intramolecular reaction of the number 12 hydroxy with chlorine and the ultimate formation of a keto-group at the number 12 position all take place as a single step in the overall process. It is noted that once the methyl 7α-hydroxy-3α-(m-iodophenylacetoxy)-12-oxo-cholanate has been prepared as described above, such is then readily converted to the desired chenodeoxycholic acid in accordance with techniques known to persons skilled in the art. Specifically, referring once again to Sato et al at page 1368, a procedure is set forth wherein the 12-oxo derivative is dissolved in ethanedithiol and then boron fluoride ethyl ether added to the resulting solution. After allowing to stand for a short period, 1N sodium hydroxide was added while cooling in an ice bath and the mixture extracted with ether. The ethereal solution was washed with dilute sodium hydroxide and water and dried over anhydrous sodium sulfate. After removal of the solvent, the residual solid crystallized from methanol as plates of methyl 3α,7α-diacetoxy-12-oxocholanate 12-ethylenethioketal. The thioketal was dissolved in absolute ethanol and refluxed for 8 hr with Raney nickel. After removal of the catalyst by filtration and removal of the solvent in vacuo, a residue of fine needles was obtained which, upon recrystallization from methanol, yielded needles of methyl chenodeoxycholate diacetate. The diacetate was hydrolyzed with ethanolic 5% potassium hydroxide for 4 hr. After partial concentration of the volume and addition of water, the reaction produce was acidified with hydrochloric acid. The resulting precipitate was collected, dried, and crystallized from ethyl acetate. A quantitative crop of prisms were obtained which, upon recrystallization from the same wsolvent, yielded a chenodeoxycholic acid product.

Yet another procedure for preparing product chenodeoxycholic acid from the 12-oxo derivative such as described above is set forth in Iida et al, J. Org. Chem., Vol. 46, No. 13 (1981). In general, the conversion of the 12-oxo derivative to chenodeoxycholic acid proceeds in three steps as follows:

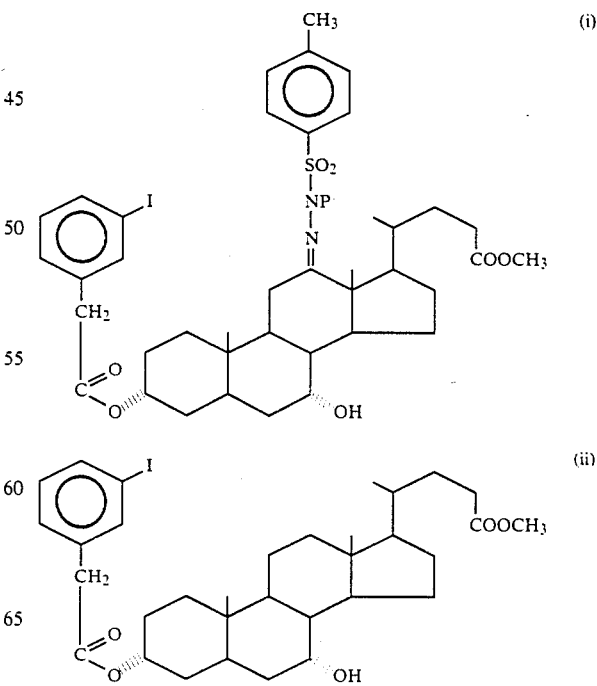

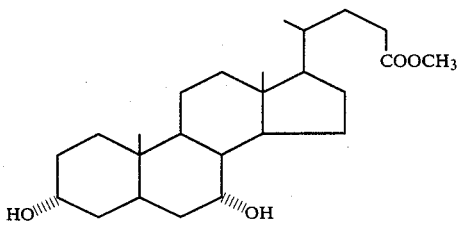

The above reaction sequence, as previously indicated, involved the initial reaction of m-iodophenylacetyl chloride with cholic acid methyl ester. It will be appreciated, however, that other iodophenyl halides falling within the formula (I) above are also suitable. Furthermore, when m-dichloroiodophenylacetyl chloride is employed instead of m-iodophenylacetyl chloride, it will not be necessary to carry out the chlorination step described above.

By virtue of the above process, crystals of chenodeoxycholic acid of about 95% or greater purity are recovered. The percent yield, based on the conversion of cholic acid methyl ester to methyl 7α-hydroxy-3α-(m-iodophenylacetoxy)-12-oxo cholanate is about 80–85% which represents a significant improvement over the 40 to 45% yield typifying prior art techniques based on the same conversion. Additionally, unlike the processes of the prior art, the process described above at no point uses highly toxic compounds such as dichromate or chromium trioxide which required extraordinary precautionary measures for their use and disposal.

The following examples are given in order to illustrate the preferred embodiment of the invention and should in no way be construed as encompassing the entire breadth of the invention.

EXAMPLE

There were dissolved in 22 ml of dry benzene and 20 ml of pyridine 42.3 g of cholic methyl ester and 33.7 g of m-iodophenylacetyl chloride. The mixture was heated under nitrogen for 8 hours. The solvent was removed in a rotary evaporator and a methyl 3α-(m-iodophenylacetoxy)-7α,12α-dihydroxy cholanate product crystallized from CH$_2$CH$_2$-hexane.

There were then dissolved, in 500 ml of carbon tetrachloride at 0° C., 6.7 g of the crystallized product. Chlorine gas was bubbled into the solution until a total amount of 1.5 g had been added. The resulting mixture was stirred for 20 minutes at 0°–5° C. To the mixture was then added 0.04 ml of pyridine, atmospheric moisture being excluded during this process. The reaction mixture was allowed to stand at room temperature for 30 minutes, and the solution was then treated with an aqueous sodium thiosulfate solution to form a 5% solution. The previously clear yellow reaction mixture became almost colorless. The layer of carbon tetrachloride was separated and washed, subsequently with dilute hydrochloric acid and with water and, after drying the solvent, was evaporated to obtain methyl 7α-hydroxy-3α-(m-iodophenyl acetoxy) 12-oxocholanate.

There was then added to 200 ml of acetic acid, while stirring, 13.4 g of the 12 oxocholanate obtained above. Added gradually were 7.5 g of p-toluenesulfonylhydrazide. The reaction mixture was allowed to stand for 12 hours at room temperature and was then diluted with water and extracted with methylene dichloride. After washing with 5% sodium bicarbonate solution to obtain a neutral solution, the solvent was evaporated therefrom.

The residue was dissolved in 280 ml of acetic acid while stirring. There were then added to the resulting solution 5.5 g of sodium borohydride at a rate which did not allow the reaction temperature to exceed 60° C. Stirring was continued at room temperature for 3 hours. The flask was immersed in an ice bath and ice chips were gradually stirred into the solution. The resulting precipitate was filtered and hydrolyzed to yield chenodeoxycholic acid in a yield of 30–35% based on conversion from the cholic acid methyl ester starting reagent, as opposed to the 17% yield according to the prior art.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A compound of the formula:

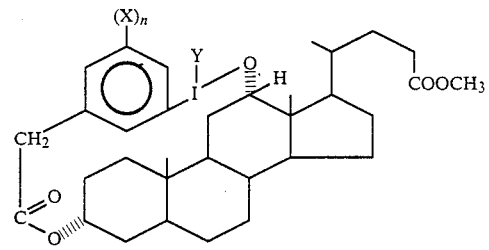

wherein —X is an electron withdrawing group, n is an integer equal to zero or one, and —Y is a halogen.

2. The compound of claim 1 wherein —X is —NO$_2$ or a halogen.

3. The compound of claim 1 wherein —Y is chlorine.

4. The compound of claim 3 wherein n is equal to zero.

5. A compound of the formula:

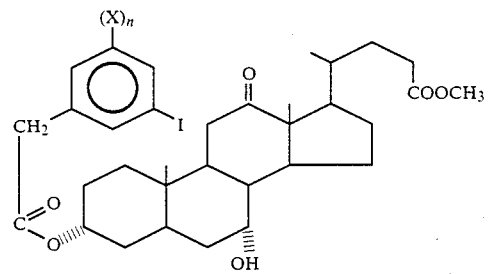

wherein —X is an electron withdrawing group and n is an integer equal to zero or one.

6. The compound of claim 5 wherein —X is NO$_2$ or a halogen.

7. A process for producing a compound of the formula:

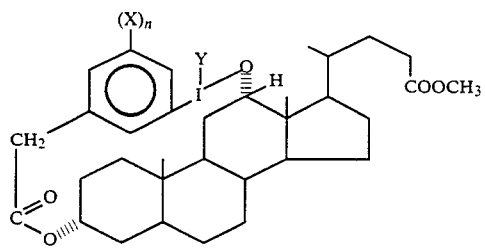

comprising the steps of:

(i) reacting 5β-cholanic acid-3α,7α,12α-triol methyl ester with a compound of the formula:

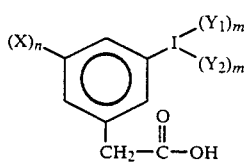

wherein —X is an electron withdrawing group, n is an integer equal to zero or one, —$Y_1$ and —$Y_2$, which are identical or different, are each a halogen, and m is an integer equal to zero or one;

there being formed, when m equals zero, a compound of the formula:

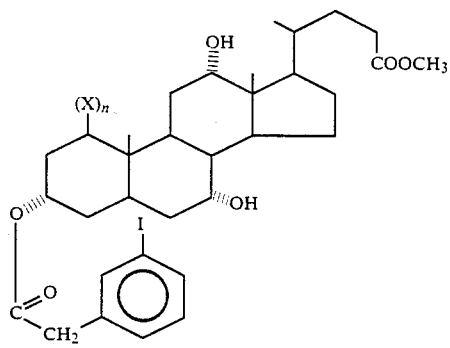

said compound (II) then being reacted with a halogen source to form a compound of the formula:

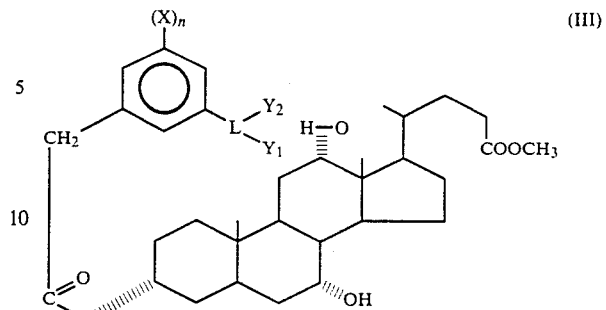

there being formed, when m equals one, said compound (III);

(ii) reacting the group —$Y_1$ or —$Y_2$ of said compound (III) with the number twelve carbon of said compound (III), in the presence of a solvent serving as an acid scavenger, to form said compound (IV).

8. The process of claim 7 wherein —X is a halogen or —$NO_2$.

9. The process of claim 7 wherein —$Y_1$ and —$Y_2$ are chlorine.

10. The process of claim 7 wherein m equals zero and wherein said compound (II) is reacted with molecular chlorine in a carbon tetrachloride solvent.

11. The process of claim 7 wherein said solvent serving as an acid scavenger is pyridine.

12. The process of claim 7 further comprising
removing from said compound (IV), in the presence of an acid scavenger, an additional hydrogen halide to form methyl 7α-hydroxy-3α-(m-iodophenylacetoxy)-12-oxo cholanate.

13. The process of claim 12 further comprising
reacting said methyl 7α-hydroxy-3α-(m-iodophenyl acetoxy)-12-oxo cholanate with p-toluenesulfonyl hydrazide to yield methyl 7α-hydroxy-3α-(m-iodophenyl acetoxy)-12-oxo cholanate tosyl hydrazone;

reacting said methyl 7α-hydroxy-3α-(m-iodophenyl acetoxy)-12-oxo cholonate tosyl hydrazone with sodium borohydride to yield yield methyl 7α-hydroxy-3α-(m-iodophenylacetoxy)chenodeoxycholate; and hydrolyzing said 7α-hydroxy-3α-(m-iodophenylacetoxy)chenodeoxycholate to chenodeoxycholic acid.

* * * * *